United States Patent [19]
Itoh

[11] 4,285,699
[45] Aug. 25, 1981

[54] ANALYTICAL METHOD AND APPARATUS FOR THE DETERMINATION OF TOTAL NITROGEN CONTENTS IN SAMPLES

[75] Inventor: Tadamasa Itoh, Toyonaka, Japan

[73] Assignee: Sumitomo Chemical Company, Limited, Osaka, Japan

[21] Appl. No.: 150,693

[22] Filed: May 16, 1980

[30] Foreign Application Priority Data

May 23, 1979 [JP] Japan .................................. 54-64473

[51] Int. Cl.³ .................... G01N 33/18; G01N 27/18; G01N 31/10; G01N 31/12
[52] U.S. Cl. .............................. 23/230 PC; 23/232 R; 23/232 C; 422/78; 422/80
[58] Field of Search .......... 23/230 PC, 232 R, 232 C; 422/78, 80

[56] References Cited

U.S. PATENT DOCUMENTS

| | | | |
|---|---|---|---|
| 3,304,159 | 2/1967 | Hinsvark | 422/78 |
| 4,066,402 | 1/1978 | Komiyama et al. | 23/230 PC |
| 4,070,155 | 1/1978 | Fraim | 23/230 PC |
| 4,095,949 | 6/1978 | Flett | 23/230 PC |

*Primary Examiner*—Ronald Serwin
*Attorney, Agent, or Firm*—Birch, Stewart, Kolasch & Birch

[57] ABSTRACT

An analytical method for the determination of total nitrogen contents in samples, which comprises passing an inert gas stream containing substantially no nitrogen through a first reaction tube which is packed with a decomposition catalyst and oxidizing agent and maintained at a temperature of 700° to 1100° C., a condenser for condensing unnecessary components in the gaseous products from the first reaction tube, a second reaction tube which is packed with an oxidizing agent and a reducing agent and is maintained at a temperature of 400° to 800° C., a moisture-absorbing tube and a carbon dioxide gas-absorbing tube in this order, introducing a liquid sample to be analyzed into the first reaction tube and sending nitrogen gas coming out of the carbon dioxide gas-absorbing tube to a nitrogen gas analyzer to determine the nitrogen gas, and an apparatus for carrying out such a method.

10 Claims, 3 Drawing Figures

ANALYTICAL METHOD AND APPARATUS FOR THE DETERMINATION OF TOTAL NITROGEN CONTENTS IN SAMPLES

BACKGROUND OF THE INVENTION

1. Field of the Invention

The present invention relates to an analytical method for the determination of the total nitrogen content, principally, in non-aqueous and aqueous liquid samples, and an apparatus suitable for the above analytical method. In view of air pollution caused by nitrogen oxides and nutritional enrichment of water, it has recently become important to determine the nitrogen content of fuel oils, waste water and environmental water.

2. Description of the Prior Art

For analyzing a trace amount of nitrogen in liquid or solid samples, Kjeldahl method, Dumas method and ter Muelen method have hitherto been used. Among these methods, Kjeldahl method has been used with popularity in various fields. This method is superior as a chemical analytical method, but because of its troublesome operations, high grades of technique and skill are required in order for analyzers to obtain accurate analytical values. Moreover, there is too much difficulty in mechanizing this method in order to complete the determination within several minutes, and an apparatus which can be operated simply and rapidly has not yet been developed.

The Dumas method is useful for the determination of nitrogen gas produced by combustion, oxidation and reduction using a mixture of an inert gas and oxygen gas, and it has been simplified by the development of an elementary analyzer for C-H-N. But the analyzer is not suitable for nitrogen microanalysis because its lowest limit of determinable nitrogen content is as high as 0.2% and its sensitivity is insufficient. Besides, apparatuses for nitrogen micro-analysis have been developed by combining the Dumas method and a gas chromatograph with a thermal conductivity detector. However, because oxygen gas is used in these apparatuses, the reducing agents used therein have a shorter life. Furthermore, the apparatuses are complicated in structure and are expensive in cost.

Nitrogen can be determined with a high sensitivity by combining colormetric titration or electro-conductometry with the Muelen method which converts nitrogen compounds to ammonia by hydrogenolysis. Since, however, this combined method uses a large quantity of hydrogen at a high temperature, there is a safety problem in the operation thereof. Moreover, the reduction catalysts lose their activity within a short period of time, and hence, they must frequently be re-activated. Furthermore, this method has a drawback that in case of nitrogen compounds easily decomposable to nitrogen gas such as azo compounds, it shows a slightly smaller value of nitrogen contents than the theoretical value.

There has also been developed an analyzer suitable for the simple and rapid determination of nitrogen. According to this analyzer, an aqueous sample is introduced onto a palladium catalyst heated at a high temperature to bring water molecules into a highly activated state, and the activated water molecules convert nitrogen compounds in the sample to nitrogen gas by their oxidative and reductive actions. But, this analyzer can not be applied to non-aqueous samples.

SUMMARY OF THE INVENTION

In view of the drawbacks of the conventional analytical methods and apparatuses, the present inventors have conducted extensive studies to find an improved analytical method and apparatus which are free from the drawbacks of the prior art and which are capable of determining even a trace amount of total nitrogen contained not only in aqueous samples but also in non-aqueous ones. As a result, it has been found that the desired determination of nitrogen can be carried out safely, simply, rapidly and accurately at a low cost by using a first reaction tube packed with a decomposition catalyst and an oxidizing agent and a second reaction tube packed with an oxidizing agent and a reducing agent.

An object of the present invention is to provide an improved analytical method for determining a trace amount of total nitrogen in samples. Another object of the invention is to provide an analytical method for determining total nitrogen particularly in non-aqueous samples. A further object of the invention is to provide an apparatus suitable for the analytical method as set forth above. These and other objects and advantages of the invention will be apparent to those skilled in the art from the following description.

According to the present invention, the desired determination of total nitrogen content in samples can be carried out by passing an inert gas stream containing substantially no nitrogen through a first reaction tube which is packed with a decomposition catalyst and an oxidizing agent and maintained at a temperature of 700° C. to 1100° C., a condenser for condensing unnecessary components in the gaseous products from the first reaction tube, a second reaction tube which is packed with an oxidizing agent and a reducing agent and maintained at a temperature of 400° to 800° C., a moisture-absorbing tube and a carbon dioxide gas-absorbing tube in this order. The sample to be analyzed is introduced into the first reaction tube and nitrogen gas coming out from the carbon dioxide gas-absorbing tube is sent to to a nitrogen gas analyzer to determine the nitrogen gas content. The apparatus useful for the determination of total nitrogen comprises a means for feeding an inert gas containing substantially no nitrogen, a means for feeding a sample, the first reaction tube packed with a decomposition catalyst and an oxidizing agent and maintained at a temperature of 700° to 1100° C., a condenser for condensing unnecessary components in the gaseous products from the first reaction tube, the second reaction tube packed with an oxidizing agent and a reducing agent and maintained at a temperature of 400° to 800° C., a moisture-absorbing tube, a carbon dioxide gas-absorbing tube, a nitrogen gas detector, conduits connecting these means and a data treatment means.

According to the analytical method of the present invention, nitrogen compounds in the sample are converted into nitrogen gas on the decomposition catalyst which is heated at a high temperature in an inert gas stream and organic compounds are completely oxidized with the oxidizing agent in the first reaction tube. The gaseous products (e.g. $H_2O$, $CO_2$, $N_2$, $O_2$, $H_2$, etc.) from the first reaction tube are condensed in the condenser; the hydrogen gas and oxygen gas in the gaseous products thus condensed are removed by the oxidizing agent and reducing agent in the second reaction tube; and further moisture and carbon dioxide are removed with the moisture-absorbing tube and carbon dioxide gas-absorbing tube; and then nitrogen gas only is introduced into the nitrogen gas analyzer to determine the amount of the nitrogen gas.

Preferred inert gases used in the present invention are helium and argon.

The decomposition catalyst includes quartz wool and/or silica alumina ceramics wool, which is usually packed onto an oxidizing agent and used at 700° to 1100° C. If the decomposition catalyst is not packed onto the oxidizing agent and a sample is directly passed through the oxidizing agent of metal oxide, nitrogen compounds are converted into nitrogen gas and nitrogen oxide gas in different ratios, which are dependent upon the kinds of the nitrogen compounds. Since both gases are different from each other in polarity, they are different in the velocity at which they reach the reducing agent. Consequently, nitrogen gas produced in the oxidizing agent zone and nitrogen gas produced by reduction in the reducing agent zone require a different time in which to reach the detector, which results in poor determinability and reproducibility. When quartz wool and/or silica alumina ceramics wool are used as a decomposition catalyst, any kinds of nitrogen compounds are wholly converted into nitrogen gas on the catalyst layer, by which the desired determination of nitrogen content can be carried out with excellent determinability and reproducibility. Of the foregoing decomposition catalysts, silica alumina ceramics wool is particularly preferred.

The oxidizing agent is not always necessary for the analysis of aqueous samples, but when non-aqueous samples are analyzed, the oxidizing agent enables the determination a trace amount of nitrogen with good reproducibility by previously oxidizing an organic solvent into carbon dioxide gas and water using the agent and then passing through the decomposition catalyst. As the oxidizing agent, for example copper oxide, tricobalt tetraoxide and chromium oxide are preferably used.

The condenser, generally called a "trap", has a form of U-shaped glass tube or double glass tube, and it acts to condense water vapor, condensable products and the like from the decomposition catalyst zone. The gases from the condenser are sent to the oxidation/reduction tube (the second reaction tube) and subsequently to the moisture-absorbing tube wherein water vapor untrapped by the condenser and water vapor produced in the oxidiation/reduction tube are removed.

The moisture absorber used in the present invention includes magnesium perchlorate, calcium chloride and molecular sieve which are widely used in the common elementary analysis. However, magnesium perchlorate and calcium chloride tend to deliquesce and agglomerate on absorbing moisture. When they absorb moisture they block the carrier gas stream. As a result, a desiccant can only partly be used and can hardly be used for a long period of time so that the desiccant should frequently be exchanged. On the other hand, molecular sieve causes no such blockade even when it absorbs moisture, but when used for a long time, it has an undesirable effect on the accurate micro-analysis, because it varies in the absorption and release of component gases with the progress of moisture absorption. In order to prevent such an undesirable blockade of carrier gas stream by moisture absorption, it is preferable to use a mixture of magnesium perchlorate and a blockade inhibitor of 30 to 75 v/v % based on the total volume of the mixture. Suitable example of the blockade inhibitor are sulfonic acid type ion-exchange resins used for desiccation, that is, ion-exchange resins having —$SO_3^-$ group as a ion-exchange group, which are commercially available. Another advantage of this mixture is to make it possible to accurately follow the progress of moisture absorption by change in color.

The gas obtained after passing through the moisture-absorbing tube is introduced into the nitrogen gas detector through the carbon dioxide gas-absorbing tube. Nitrogen gas can be detected by the conventional thermal conductivity method, helium ionization method, mass analysis or discharge spectrum method. When a gas chromatograph with a thermal conductivity detector is used, helium or argon gas is used as a carrier gas, and nitrogen gas generated at the reaction portion is detected. When a gas chromatograph with a helium ionization detector is used, helium gas having an extremely high purity is used as a carrier gas, and nitrogen gas generated at the reaction portion can be detected with a high sensitivity by ionizing or exciting helium by $\beta$-rays or glow discharge, ionizing the nitrogen gas by the Penning effect and measuring electrically the increment of ionic current.

In the mass analysis, helium or argon is used as a carrier gas, and it is desirable to determine nitrogen gas generated at the reaction portion by mass fragmentgraphy at $m/e=28$ on a mass spectrometer. In the nitrogen detection with discharge spectrum, argon gas is used as a carrier gas, and nitrogen gas generated at the reaction portion can be detected with a high sensitivity by introducing the nitrogen gas into the detection cell, generating discharge by applying a high voltage to electrodes at the both sides of the cell to obtain the emission spectrum, separating only a ray having a wavelength of 3371 Å from the spectrum through an optical filter and detecting electrically the ray with a photomultiplier.

The method of the present invention will be illustrated in more detail in case of using a gas chromatograph with a thermal conductivity detector with reference to the accompanying drawing.

Figure 1:
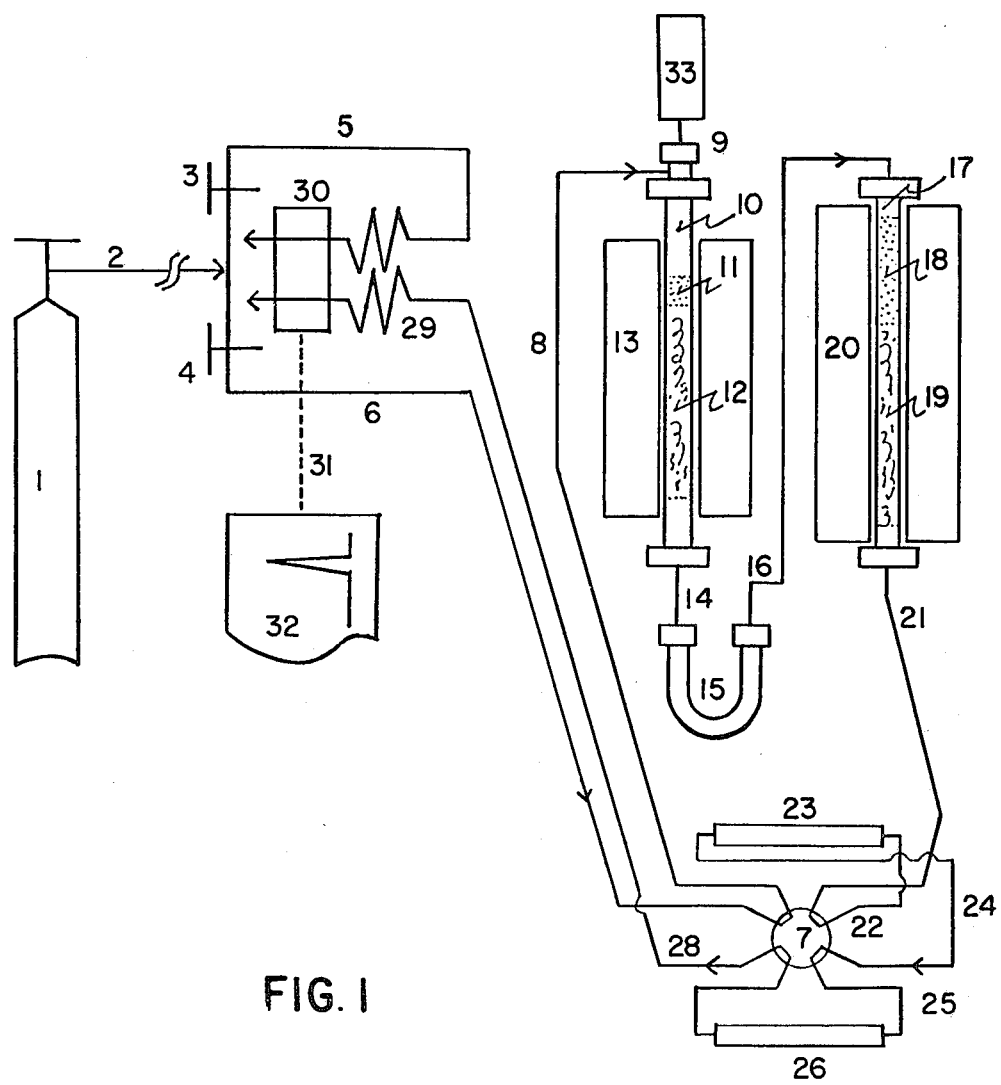
FIG. 1 shows a schematic diagram illustrating one embodiment of apparatus for carrying out the method of the present invention.

In FIG. 1 showing a schematic diagram of one embodiment of the present apparatus, 1 is a carrier gas bomb which contains helium or argon as a carrier gas. The carrier gas passes through a pipe 2 and divides into two flows. One flow passes through a pressure controller 3 and enters the reference side of a gas chromatograph. Another flow passes through a pressure controller 4, a pipe 6, a switch cock 7 and a pipe 8 in this order and then enters the first reactor 10. A proper flow rate of the carrier gas is 20 to 100 ml/min. The switch cock 7 is for connecting a reaction portion to a detection portion or separating the two portions from each other.

The first reactor 10 is made of a quartz tube (internal diameter, 10–15 mm; length, 20–30 cm), and it comprises an upper zone and a lower zone. The upper zone is packed with a decomposition catalyst 11 of quartz cotton or silica alumina ceramics wool (the thickness of the fiber is preferably 1 to 10μ). The lower zone is packed with an oxidizing agent 12 such as copper oxide, tricobalt tetraoxide or chromium oxide. For practical use, the first reactor is heated to 700° to 1100° C. by a furnace 13. An inlet 9 for injecting samples is set on the top of the first reactor, and samples are injected by a microsyringe or an automatic injector 33. Gases produced in the first reactor, for example $H_2O$, $CO_2$, $N_2$, $O_2$ and $H_2$, enter a U-shaped glass condenser 15 (internal diameter, 6–12 mm; length, 10–20 cm) to make free from water vapor and fine powders.

The gases from the condenser enter the second reactor 17 packed with an oxidizing agent 18 and a reducing agent 19. During the passing of the gases through the second reactor, hydrogen gas and oxygen gas produced in the first reactor are removed by the oxidizing agent and reducing agent, respectively. The second reactor 17 is preferably made of a quartz tube (internal diameter, 10–15 mm; length, 20–30 cm). As the oxidizing agent, tricobalt tetraoxide or copper oxide is used, and as the reducing agent, reduced copper or reduced nickel is used. The second reactor is preferably heated to 400° to 800° C. by a furnace 20.

The gases from the second reactor pass through a switch cock 7, a moisture-absorbing tube 23 and a carbon dioxide gas-absorbing tube 26 in this order and then enter a gas chromatograph equipped with a thermal conductivity detector 30. The moisture-absorbing tube is for the complete removal of moisture, and most preferably it is a glass tube (internal diameter, 8–12 mm; length, 10–20 cm) which is packed with a mixture of magnesium perchlorate and an ion-exchange resin for drying (2:1 to 1:3 by volume). The carbon dioxide gas-absorbing tube is a glass tube (internal diameter, 8–12 mm; length, 10–20 cm) which is packed with soda asbestos or soda lime.

The type of the gas chromatograph may be any one of the double-column passage and single-column passage. A separating column 29 is packed with the conventional packings which are usually used for separation of inorganic gases, for example silica gel, activated carbon, porous polymer beads and molecular sieve. Signals from the thermal conductivity detector 30 are recorded on a recorder 32 through a signal line 31. The portions described above are connected by pipes 2, 5, 6, 8, 14, 16, 21, 22, 24, 25, 27 and 28.

The present invention will be illustrated by the following examples, which are however not to be interpreted as limiting the invention thereto.

EXAMPLE 1

Determination was carried out using the apparatus shown in FIG. 1. The first reactor was made of a quartz tube (external diameter, 15 mm; internal diameter, 13 mm; length, 250 mm), and it comprised three zones in contact with one another. The lowest zone was packed with quartz wool and its height was 30 mm from the bottom. The middle zone was packed with 0.6 mm copper oxide wire (length, 2–4 mm) and its height was 120 mm. The highest zone was packed with a decomposition catalyst (quartz wool; thickness of wool fiber, 1–6μ) and its height was 20 mm. For practical use, the first reactor was heated to 850° C. by a furnace of 200 mm in length.

The second reactor was made of a quartz tube (external diameter, 15 mm; internal diameter, 13 mm; length, 250 mm), and it comprised four zones in contact with one another. The lowest zone was packed with quartz wool and its height was 30 mm from the bottom. The second zone from the bottom was packed with 0.6 mm reduced copper wire (length, 2–4 mm) and its height was 120 mm. The third zone from the bottom was packed with 10 to 20 mesh tricobalt tetraoxide and its height was 70 mm. The highest zone was packed with quartz wool and its height was 30 mm. The second reactor was heated to 600° C. by a furnace of 240 mm in length.

The condenser was made of a U-shaped glass tube (internal diameter, 8 mm; length, 150 mm). The moisture-absorbing tube was made of a straight glass tube (internal diameter, 10 mm; length, 150 mm) and packed with a 1:1 mixture of 20 to 40 mesh magnesium perchlorate and a 20 to 40 mesh sulfonic acid type ion-exchange resin for drying (Diaion® SK-1B, produced by Mitsubishi Chemical Co., Ltd.). The carbon dioxide gas-absorbing tube (internal diameter, 10 mm; length, 150 mm) was packed with 20 to 40 mesh soda asbestos. The separating column of the gas chromatograph was made of a stainless steel column (internal diameter, 3 mm; length, 0.5 m), and packed with 80 to 100 mesh activated carbon. Helium was used as a carrier gas and passed at a rate of 70 ml/min, the column temperature was 60° C., the temperature of the thermal conductivity detector was 100° C. and the bridge current was 150 mA.

Figure 2:
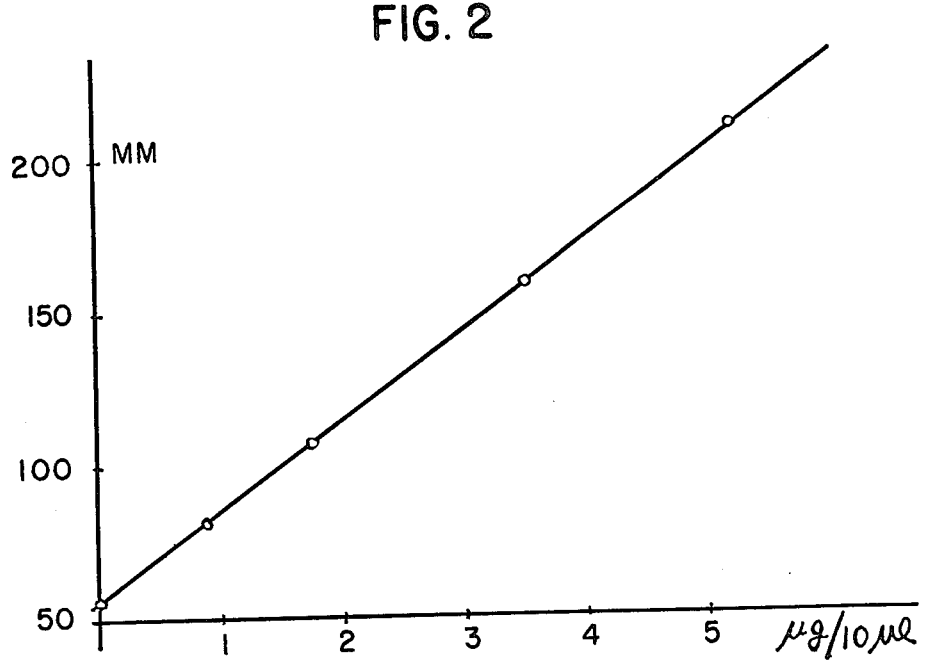
FIG. 2 shows a calibration curve obtained by injecting 10 μl of a mixture of prescribed amounts of ethyl alcohol and pyridine by means of a microsyringe.

A prescribed amount of pyridine was added to ethyl alcohol, and 10 μl of the mixture was injected by means of a microsyringe to make a calibration curve. Chromatogram was obtained in about 2 minutes, and by plotting the height of nitrogen peak against the known concentration of total nitrogen, a good straight line as shown in FIG. 2 was obtained. Various solutions of nitrogen-containing organic compounds in an organic solvent were prepared and 10 μl of each solution was injected by means of a microsyringe. The total nitrogen content was measured according to the peak height absolute calibration curve method by using pyridine as a standard. The results are shown in Table 1.

TABLE 1

| Sample | Solvent | Nitrogen content (known) (μg) | Nitrogen content (found) (μg) | | | | Detection percentage (%) |
|---|---|---|---|---|---|---|---|
| | | | No. 1 | No. 2 | No. 3 | Average | |
| Acetanilide | Ethanol | 10.00 | 10.10 | 9.96 | 9.97 | 10.01 | 100.1 |
| Acrylonitrile | Acetone | 4.25 | 4.18 | 4.20 | 4.21 | 4.20 | 98.8 |
| Azobenzene | Ethyl ether | 4.00 | 3.93 | 4.02 | 3.95 | 3.97 | 99.3 |
| Aniline | Acetic acid | 3.07 | 3.01 | 3.05 | 3.07 | 3.04 | 99.0 |
| Ammonium acetate | Methanol | 10.00 | 9.89 | 9.94 | 9.90 | 9.91 | 99.1 |
| p-Nitroaniline | Ethanol | 5.00 | 4.98 | 5.03 | 5.04 | 5.02 | 100.4 |
| Phenylhydrazine | Acetic acid | 8.00 | 8.03 | 8.00 | 8.09 | 8.04 | 100.5 |
| Urea | Ethanol | 2.00 | 2.01 | 2.02 | 2.04 | 2.02 | 101.0 |
| Thiourea | Methanol | 5.00 | 4.93 | 4.98 | 4.91 | 4.94 | 98.8 |

TABLE 1-continued

| Sample | Solvent | Nitrogen content (known) (μg) | Nitrogen content (found) (μg) | | | | Detection percentage (%) |
|---|---|---|---|---|---|---|---|
| | | | No. 1 | No. 2 | No. 3 | Average | |
| Nicotinic acid | Ethanol | 4.00 | 3.90 | 3.97 | 3.93 | 3.93 | 98.3 |
| Caffeine | Ethanol | 2.00 | 2.01 | 1.97 | 1.98 | 1.99 | 99.5 |
| m-Nitrobenzoic acid | Ethyl ether | 5.00 | 5.03 | 5.05 | 5.02 | 5.03 | 100.6 |
| DL-α-alanine | Methanol | 2.00 | 1.97 | 2.00 | 1.98 | 1.98 | 99.0 |

Figure 3:
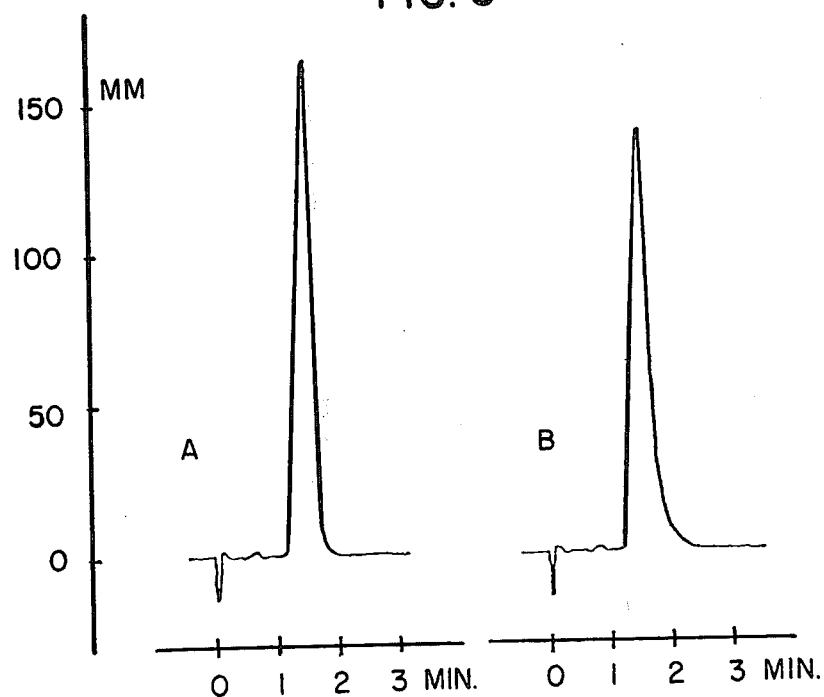
FIG. 3 shows chromatograms obtained by injecting 10 μl of a sample, a mixture of ethyl alcohol and pyridine having a total nitrogen content of 0.348 μg/μl, into the first reaction tube containing or not containing the decomposition catalyst. (a) is a chromatogram obtained by using the decomposition catalyst, and (b) is one obtained without using the decomposition catalyst.

The effect of the decomposition catalyst was examined as follows: 10 μl of a test sample, which was a mixture of ethyl alcohol and pyridine having a total nitrogen content of 0.348 μg/μl, was injected by means of a microsyringe into the first reactor containing and not containing said catalyst. FIG. 3 shows chromatograms thus obtained. (a) is a chromatogram obtained with the decomposition catalyst of quartz wool, and (b) is one obtained by directly introducing the sample into the oxidizing agent zone without using decomposition catalyst. The effect of quartz wool as decomposition catalyst was clearly observed.

EXAMPLE 2

The nitrogen content of various nitrogen-containing compounds was determined in the same manner as described in Example 1 using the following apparatus:

The first reactor was made of a quartz tube (external diameter, 15 mm; internal diameter, 13 mm; length, 250 mm), and it comprised three zones in contact with one another. The lowest zone was packed with quartz wool and its height was 20 mm from the bottom. The middle zone was packed with 0.6 mmφ copper oxide wire (length, 2-4 mm) and its height was 130 mm. The highest zone was packed with a decomposition catalyst (silica alumina ceramics wool; thickness of wool fiber, 1-5μ) and its height was 20 mm. For practical use, the first reactor was heated to 950° C. by a furnace of 200 mm in length.

The second reactor was made of n quartz tube (external diameter, 15 mm; internal diameter, 10 mm; length, 250 mm), and it comprised four zones in contact with one another. The lowest zone was packed with quartz cotton and its height was 30 mm from the bottom. The second zone from the bottom was packed with 0.6 mmφ reduced copper wire (length, 2-4 mm) and its height was 140 mm. The third zone from the bottom was packed with 0.6 mmφ copper oxide wire (length, 2-4 mm) and its height was 50 mm. The highest zone was packed with quartz cotton and its height was 30 mm. For practical use, the second reactor was heated to 550° C. by a furnace of 240 mm in length.

For analysis, a prescribed amount of the nitrogen-containing compound was dissolved in ion-exchange water, and 10 μl of the test solution was injected by means of a microsyringe. The total nitrogen content was determined according to the peak height absolute calibration curve method, by using urea as a standard. The results are shown in Table 2.

TABLE 2

| Sample | Nitrogen content (known) (μg) | Nitrogen content (found) (μg) | | | | Detection percentage (%) |
|---|---|---|---|---|---|---|
| | | No. 1 | No. 2 | No. 3 | Average | |
| Ammonium sulfate | 5.00 | 4.98 | 4.97 | 4.97 | 4.97 | 99.4 |
| Ammonium chloride | 2.00 | 1.99 | 2.01 | 1.98 | 1.99 | 99.5 |
| Diammonium hydrogen phosphate | 2.00 | 1.98 | 1.99 | 1.96 | 1.98 | 99.0 |
| Potassium nitrate | 5.00 | 5.01 | 4.98 | 4.99 | 4.99 | 99.8 |
| Sodium nitrite | 2.00 | 2.02 | 2.00 | 2.00 | 2.01 | 100.5 |
| Glycine | 2.00 | 1.97 | 1.99 | 1.99 | 1.98 | 99.0 |
| Glycylglycine | 5.00 | 5.02 | 5.00 | 5.00 | 5.01 | 100.2 |
| ε-Amino-n-caproic acid | 5.00 | 4.99 | 5.01 | 4.97 | 4.99 | 99.8 |
| ε-Caprolactam | 5.00 | 4.98 | 4.98 | 4.99 | 4.98 | 99.6 |
| Hydrazine sulfate | 10.00 | 10.04 | 10.00 | 10.03 | 10.02 | 100.2 |
| Adipic acid hydrazide | 2.00 | 1.99 | 2.00 | 2.00 | 2.00 | 100.0 |
| Hydroxylamine hydrochloride | 5.00 | 4.96 | 4.99 | 4.93 | 4.96 | 99.2 |
| Acetoxime | 5.00 | 4.90 | 4.91 | 4.91 | 4.91 | 98.2 |
| Sodium thiocyanate | 5.00 | 4.86 | 4.93 | 4.91 | 4.90 | 98.0 |
| Potassium ferricyanide | 5.00 | 5.01 | 4.99 | 4.99 | 5.00 | 100.0 |
| Hexamethylene tetramine | 5.00 | 5.03 | 5.00 | 5.01 | 5.01 | 100.2 |

The analytical method and the apparatus for the determination of total nitrogen which are described above, can widely be applied to the analysis of not only fuel oils, petrochemicals and organic synthetic products but also foods such as soy, ice cream and fruit drinks. Besides, as a nitrogen gas detector, a thermal conductivity gas chromatograph can be used which is one of the most popularly employed analytical equipments. Consequently, even a trace amount of total nitrogen can be determined cheaply, safely, simply, rapidly and accurately.

What is claimed is:

1. An analytical method for the determination of total nitrogen contents in samples, which comprises passing an inert gas stream containing substantially no nitrogen through a first reaction tube which is packed with a decomposition catalyst and an oxidizing agent and is maintained at a temperature of 700° to 1100° C., a condenser, a second reaction tube which is packed with an oxidizing agent and a reducing agent and is maintained at a temperature of 400° to 800° C., a moisture-absorbing tube and a carbon dioxide gas-absorbing tube in this order, introducing a sample to be analyzed into the first reaction tube and sending nitrogen gas coming out of the carbon dioxide gas-absorbing tube to a nitrogen gas analyzer to determine the nitrogen gas.

2. An analytical method according to claim 1, wherein the decomposition catalyst packed in the first reaction tube is quartz wool or silica alumina ceramics wool.

3. An analytical method according to claim 2, wherein the decomposition catalyst is silica alumina ceramics wool.

4. An analytical method according to claim 1, wherein the moisture absorber packed in the moisture-absorbing tube is a mixture of magnesium perchlorate and an ion-exchange resin for drying in a volume ratio of 2:1 to 1:3.

5. An analytical method according to claim 1, wherein said inert carrier gas is helium or argon.

6. An analytical method according to claim 1, wherein nitrogen is determined by gas chromatography.

7. An apparatus for analyzing the total nitrogen content in samples comprising: means for feeding an inert gas containing substantially no nitrogen, means for feeding samples, a first reaction tube which is packed with a decomposition catalyst and an oxidizing agent and is maintained at a temperature of 700° to 1100° C., a condenser for condensing unnecessary components in gaseous products from the first reaction tube, a second reaction tube which is packed with an oxidizing agent and a reducing agent and is maintained at a temperature of 400° to 800° C., a moisture-absorbing tube, a carbon dioxide gas-absorbing tube, a nitrogen gas detector, conduits connecting these means and a data treatment means.

8. An apparatus according to claim 7, wherein the decomposition catalyst packed in the first reactor tube is quartz wool or silica alumina ceramics wool.

9. An apparatus according to claim 8, wherein the decomposition catalyst is silica alumina ceramics wool.

10. An apparatus according to claim 7, wherein the moisture absorber packed in the moisture-absorbing tube is a mixture of magnesium perchlorate and an ion-exchange resin for drying in a volume ratio of 2:1 to 1:3.

* * * * *